(12) United States Patent
Mueckter

(10) Patent No.: US 9,463,054 B2
(45) Date of Patent: Oct. 11, 2016

(54) IMPLANT SYSTEM FOR BONE FIXATION

(75) Inventor: Helmut Mueckter, Aachen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 169 days.

(21) Appl. No.: 14/360,448

(22) PCT Filed: Nov. 25, 2011

(86) PCT No.: PCT/EP2011/005944
§ 371 (c)(1),
(2), (4) Date: Jul. 30, 2014

(87) PCT Pub. No.: WO2013/075730
PCT Pub. Date: May 30, 2013

(65) Prior Publication Data
US 2014/0378973 A1 Dec. 25, 2014

(51) Int. Cl.
*A61B 17/74* (2006.01)
*A61B 17/72* (2006.01)
*A61B 17/80* (2006.01)

(52) U.S. Cl.
CPC .......... *A61B 17/744* (2013.01); *A61B 17/72* (2013.01); *A61B 17/7241* (2013.01); *A61B 17/746* (2013.01); *A61B 17/809* (2013.01); *A61B 17/8061* (2013.01)

(58) Field of Classification Search
CPC A61B 17/72; A61B 17/7241; A61B 17/744; A61B 17/746; A61B 17/8061; A61B 17/809; A61B 17/1721; A61B 17/1725
USPC .......... 606/62–68, 70, 71, 74, 75, 280–331; 623/18.11
See application file for complete search history.

(56) References Cited

U.S. PATENT DOCUMENTS 4,733,654 A * 3/1988 Marino .............. A61B 17/1721
606/64
5,356,410 A * 10/1994 Pennig ................ A61B 17/744
606/281

(Continued)

FOREIGN PATENT DOCUMENTS

EP 1398000 A1 3/2004
WO 03030749 A1 4/2003

(Continued)

OTHER PUBLICATIONS

International Preliminary Report on Patentability for Application No. PCT/EP2011/005944 dated Sep. 24, 2013.

(Continued)

*Primary Examiner* — Pedro Philogene
(74) *Attorney, Agent, or Firm* — Lerner, David, Littenberg, Krumholz & Mentlik, LLP

(57) ABSTRACT

An implant system for fixation of bone includes an intramedullary nail, an extramedullary plate, and a bone fastener. The intramedullary nail has a connecting opening defining a first axis and a transverse opening defining a second axis and is configured to receive the bone fastener. The bone fastener is configured to penetrate a first through opening of the extramedullary plate and the transverse opening of the intramedullary nail. The implant system comprises a connecting fastener to fasten the extramedullary plate to the intramedullary nail by insertion through the second through opening of the extramedullary plate and the connecting opening of the intramedullary nail. The first axis is oblique with respect to a longitudinal axis of the intramedullary nail and parallel to the second axis of the transverse opening. Thus, the extramedullary plate can move parallel to the longitudinal axis of the bone fastener towards the intramedullary nail.

29 Claims, 8 Drawing Sheets

(56) References Cited

U.S. PATENT DOCUMENTS

| | | | |
|---|---|---|---|
| 7,632,272 B2 | 12/2009 | Munro et al. | |
| 2007/0219636 A1* | 9/2007 | Thakkar | A61B 17/1721 623/18.11 |
| 2008/0154311 A1 | 6/2008 | Staeubli | |
| 2009/0164026 A1 | 6/2009 | Mikami et al. | |
| 2010/0063504 A1 | 3/2010 | Munro et al. | |
| 2013/0261622 A1* | 10/2013 | Bonjour | A61B 17/7233 606/64 |

FOREIGN PATENT DOCUMENTS

| | | | | |
|---|---|---|---|---|
| WO | WO03/030749 | * | 4/2003 | A61B 17/744 |
| WO | 2009021624 A1 | | 2/2009 | |
| WO | 2010031098 A2 | | 3/2010 | |
| WO | WO2010031098 | * | 3/2010 | A61B 17/744 |
| WO | 2010054363 A1 | | 5/2010 | |
| WO | WO2010/054363 | * | 5/2010 | A61B 17/744 |
| WO | 2010127460 A1 | | 11/2010 | |
| WO | 2012107056 A1 | | 8/2012 | |
| WO | 2012107226 A1 | | 8/2012 | |

OTHER PUBLICATIONS

International Search Report for Application No. PCT/EP2011/005944 dated May 23, 2012.

JM Spikav et al., "Fatigue failure of the sliding screw in hip fracture fixation: a report of time cases", J. Orthop Trauma 1991; 5(3), 325-331.

OA Surgery Reference: Sliding hip Screw, Nov. 14, 2010, 6 pages.

Stryker: Recon Nailing System, 2009, 36 pages.

* cited by examiner

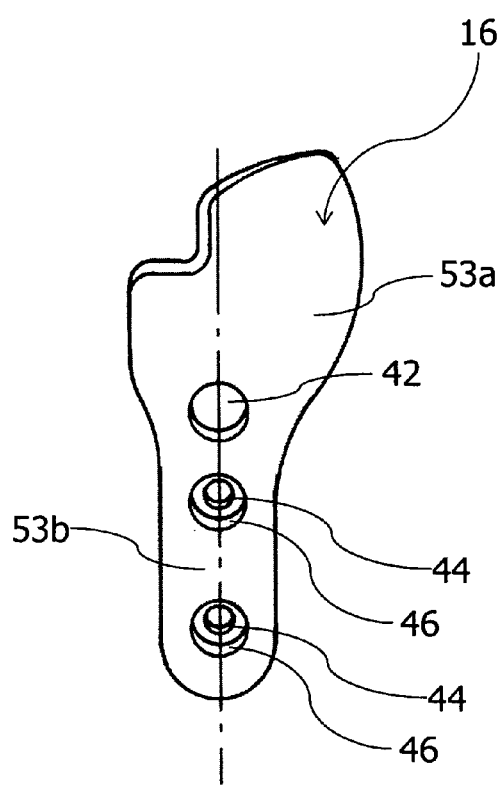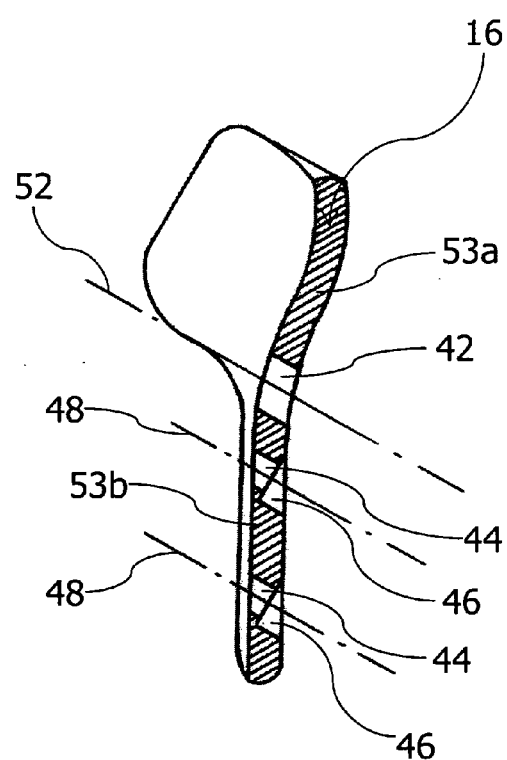
Fig. 2a
Fig. 2b

IMPLANT SYSTEM FOR BONE FIXATION

CROSS-REFERENCE TO RELATED APPLICATIONS

The present application is a national phase entry under 35 U.S.C. §371 of International Application No. PCT/EP2011/005944 filed Nov. 25, 2011, published as WO 2013/075730 A1, the disclosure of which is hereby incorporated herein by reference.

TECHNICAL FIELD

The present disclosure generally relates to an implant system for use in orthopaedic surgery. Specifically, the disclosure relates to an implant system comprising an intramedullary nail and an extramedullary plate connectable thereto for fixation of bone.

BACKGROUND

Trochanteric and subtrochanteric femur fractures are currently treated with an intramedullary nail having a transverse bore for receiving a bone fastener, such as a femoral neck screw usually provided in the form of a sliding screw. The intramedullary nail is fitted in the intramedullary canal of the femur, and the sliding screw is then passed through the transverse bore of the intramedullary nail, through the neck of the femur and into the femoral head.

The treatment of unstable trochanteric and intertrochanteric fractures, which show an additional basocervical (lateral femoral neck) fracture in combination with an avulsion of the greater trochanter, are still a challenge for internal fixation with a proximal femoral nail. With conventional surgical techniques there is no procedure to avoid a lateralization of the greater trochanter in proximal femoral nailing. To prevent lateralization of the greater trochanter, an additional stabilization is required. Such stabilization may be realized by a trochanter stabilization plate which allows for fixation of an avulsed greater trochanter fragment.

US 2007/0219636 A1 discloses an implant system for proximal femur fractures. The implant system includes an intramedullary nail and an extramedullary buttress plate. The extramedullary plate has an upper transverse part including holes for fastening the plate by screws to the greater trochanter of a femur. The plate further has a lower elongate vertical part with two central holes for receiving proximal sliding hip pins which penetrate proximal holes of the intramedullary nail for compression of bone fragments. A lower part of the plate has small holes for receiving cortical screws to fix the plate to bone. Thus, the extramedullary buttress plate is connected to the intramedullary nail only with the sliding hip pins, resulting in a low construct stability between the pins, screws and plate.

Each of US 2008/0154311 A1 and EP 1 398 000 B1 relates to an implant system with an extramedullary plate and an intramedullary nail. The plate has several openings for receiving bone screws and is fixed to the intramedullary nail by one locking screw inserted through a central through opening of the plate. Then, fixation pins or screws are inserted at different angles to each other into bone through the other holes of the extramedullary plate.

The conventional implant systems have several drawbacks. For example, when the extramedullary plate is tightened with locking screws, a sliding screw inserted through the plate and the intramedullary nail may get jammed, which would cause a canting of the extramedullary plate and the bone screws, since the axes of the bone screws are oblique to each other. Thus, the stability between the extramedullary plate, the bone screws and the intramedullary nail is decreased and a defined sliding of the sliding screw within the intramedullary nail cannot be guaranteed.

SUMMARY

Aspects of the present disclosure are directed to providing an implant system facilitating the surgical procedure and fixation of an extramedullary plate to an intramedullary nail, and increasing the stability between the plate, the intramedullary nail and corresponding fasteners.

According to one aspect, there is provided an implant system for use in orthopaedic surgery for fixation of bone. The implant system comprises an intramedullary nail, an extramedullary plate, and a bone fastener. The intramedullary nail has a connecting opening defining a first axis and a transverse opening defining a second axis and configured to receive the bone fastener. The extramedullary plate has a first through opening and a second through opening. The bone fastener is configured to penetrate the first through opening of the extramedullary plate and the transverse opening of the intramedullary nail. Further, the implant system comprises a connecting fastener configured to fasten the extramedullary plate to the intramedullary nail, the connecting fastener being adapted to be inserted through the second through opening of the extramedullary plate and the connecting opening of the intramedullary nail, wherein the first axis of the connecting opening of the intramedullary nail is oblique with respect to a longitudinal axis of the intramedullary nail and is substantially parallel to the second axis of the transverse opening of the intramedullary nail.

The implant system may be configured such that the transverse opening of the intramedullary nail is capable of receiving the bone fastener within a defined angular range with respect to the longitudinal axis of the intramedullary nail.

The implant system may in certain implementations be configured such that the first axis of the connecting opening of the intramedullary nail is substantially parallel to a longitudinal axis of the bone fastener in an implanted state. Thus, the extramedullary plate can in certain implementations move in a direction substantially parallel to the longitudinal axis of the bone fastener towards the intramedullary nail (e.g., upon implantation).

In one implementation, each of the first axis of the connecting opening and the second axis of the transverse opening defines an angle with respect to the longitudinal axis of the intramedullary nail. In the aspect described above, the angle may be within an angular range from about 90° to about 150° with respect to the longitudinal axis of the intramedullary nail. The angular range can also be between about 110° to about 140° with respect to the longitudinal axis of the intramedullary nail. Thus, the implant system may be configured such that the transverse opening of the intramedullary nail is capable of receiving the bone fastener at a defined angle or angular range, wherein the longitudinal axis of the bone fastener is substantially parallel to the first axis of the connecting opening. A surgeon may thus select a defined insertion angle of the fasteners with respect to the longitudinal axis of the intramedullary nail.

In one realization, the connecting opening of the intramedullary nail may have an internal thread configured to engage the connecting fastener. In this case, the connecting fastener may have a complementary external thread which mates with the internal thread of the connecting opening. The connecting opening of the intramedullary nail may have a conical portion or, e.g., a spherical portion on a side facing the extramedullary plate. The connecting opening may generally have a circular or elongated shape.

Like the connecting opening, the transverse opening, the first through opening and/or the second through opening may have a circular shape. In alternative configurations, one or more of those openings may be realized as elongated openings. The second through opening of the extramedullary plate may have a receiving portion for receiving a head of the connecting fastener. The receiving portion of the second through opening may be circular, conical or spherical.

In one implementation, the extramedullary plate may be anatomically pre-formed. The extramedullary plate may be curved (e.g., in accordance with the shape of the greater trochanter). The connecting fastener may be a locking screw (e.g., a cortical screw). The bone fastener may be a sliding screw, e.g., a lag screw.

In one realization, the second through opening of the extramedullary plate may define an axis which is substantially parallel to or congruent (i.e., coaxial) with the first axis defined by the connecting opening of the intramedullary nail. Moreover, the second through opening of the extramedullary plate may define an axis that is oblique with respect to a surface region of the extramedullary plate surrounding the second through opening. The second axis defined by the transverse opening of the intramedullary nail may be substantially parallel to or congruent (i.e., coaxial) with a longitudinal axis of the bone fastener.

In the aspect described above, the extramedullary plate may comprise at least one guiding structure defining an axis and configured to be received by the transverse opening of the intramedullary nail. The axis of the guiding structure may be substantially parallel to the longitudinal axis of the inserted bone fastener and/or substantially parallel to the first axis defined by the connecting opening of the intramedullary nail. In this case, the guiding structure may include a hollow portion and the bone fastener may be configured to penetrate the guiding structure of the extramedullary plate through the hollow portion. The hollow portion of the guiding structure can be connected to the first through opening of the extramedullary plate. Further, the first axis defined by the transverse opening of the intramedullary nail may be substantially parallel to the longitudinal axis of the bone fastener. In one implementation, the bone fastener may be configured to centrally penetrate the guiding structure or the hollow portion thereof. Moreover, the guiding structure may have an opening configured to receive a set screw or pin.

The extramedullary plate may comprise multiple second through openings. In a similar manner the intramedullary nail may comprise multiple connecting openings. Thus, the extramedullary plate may be fastened to the intramedullary nail using multiple connecting fasteners.

The extramedullary plate may comprise multiple first through openings. In a similar manner the intramedullary nail may comprise multiple transverse openings configured to receive bone fasteners.

According to a further aspect, there is provided an implant system for use in orthopedic surgery for fixation of bone. The implant system comprises an intramedullary nail, an extramedullary plate, and a bone fastener. The intramedullary nail has a connecting opening and a transverse opening configured to receive the bone fastener. The extramedullary plate has a first through opening and a second through opening. The bone fastener is configured to penetrate the first through opening of the extramedullary plate and the transverse opening of the intramedullary nail. Further, the implant system comprises a connecting fastener configured to fasten the extramedullary plate to the intramedullary nail, the connecting fastener being adapted to be inserted through the second through opening of the extramedullary plate and the connecting opening of the intramedullary nail, wherein the first through opening and/or the second through opening of the extramedullary plate is an elongated hole.

In case of the first through opening of the extramedullary plate is an elongated hole, the extramedullary plate can in certain implementations move in a direction substantially parallel to a first axis defined by the connecting opening towards the intramedullary nail. In case of the second through opening of the extramedullary plate is an elongated hole, the extramedullary plate can in certain configurations move in a direction substantially parallel to a longitudinal axis of the bone fastener towards the intramedullary nail.

If the first through opening of the extramedullary plate is an elongated hole, the second through opening of the extramedullary plate may be a circular hole. If the second through opening of the extramedullary plate is an elongated hole, the first through opening of the extramedullary plate may be a circular hole.

In the aspect described above, a first axis defined by the connecting opening of the intramedullary nail may be perpendicular with respect to a longitudinal axis of the intramedullary nail.

In one implementation, the elongated hole (i.e., the first through opening) of the extramedullary plate may be defined by two circular shaped openings and an elongated opening therebetween. The elongated opening of the elongated hole may have a constant width and may extend in a direction substantially parallel to a longitudinal axis of the extramedullary plate. The two circular shaped openings may be connected to the elongated opening at respective ends thereof. In other words, each side of the elongated opening, in longitudinal direction, may open out into one of the two circular shaped openings. Each of the circular shaped openings of the elongated hole may be defined by a diameter. The diameter of the circular shaped opening may extend in a direction substantially parallel to a transverse axis of the extramedullary plate (e.g., an axis perpendicular to the longitudinal axis of the extramedullary plate). The diameter of the circular shaped opening may equal to the width of the elongated opening. In other words, the elongated hole of the extramedullary plate may be defined by a length and a width perpendicular to the length. The length of the elongated hole may extend in a direction substantially parallel to a longitudinal axis of the extramedullary plate. The width of the elongated hole may extend in a direction substantially parallel to a transverse axis of the extramedullary plate (e.g., an axis perpendicular to the longitudinal axis of the extramedullary plate). Further, the length of the elongated hole may be spreader than the width of the elongated hole.

Further, the intramedullary nail, the connecting opening and the transverse opening thereof, the extramedullary plate, the first and second through opening thereof, the bone fastener and/or the connecting fastener may be configured as generally described above and hereinafter.

According to a further aspect, there is provided a method of fracture fixation of bone, the method comprising the steps of inserting an intramedullary nail into a marrow cavity of bone, wherein the intramedullary nail has a connecting opening defining a first axis and a traverse opening defining a second axis and configured to receive a bone fastener, inserting a bone fastener through the transverse opening of the intramedullary nail into bone for stabilization of the bone fracture, placing an extramedullary plate against the bone, the extramedullary plate having a first through opening and a second through opening, wherein the lateral end of the bone fastener is shoved through the first through opening of the extramedullary plate, and inserting a connecting fastener through the second through opening of the extramedullary plate and the connecting opening of the intramedullary nail to fasten the extramedullary plate to the intramedullary nail and/or the bone, wherein the first axis of the connecting opening of the intramedullary nail is oblique with respect to a longitudinal axis of the intramedullary nail and is substantially parallel to the second axis of the transverse opening of the intramedullary nail.

According to a further aspect, there is provided a method of fracture fixation of bone, the method comprising the steps of inserting an intramedullary nail into a marrow cavity of bone, wherein the intramedullary nail has a connecting opening and a traverse opening configured to receive a bone fastener, inserting a bone fastener through the transverse opening of the intramedullary nail into bone for stabilization of the bone fracture, placing an extramedullary plate against the bone, the extramedullary plate having a first through opening and a second through opening, wherein the lateral end of the bone fastener is shoved through the first through opening of the extramedullary plate, and inserting a connecting fastener through the second through opening of the extramedullary plate and the connecting opening of the intramedullary nail to fasten the extramedullary plate to the intramedullary nail and/or the bone, wherein the first through opening and/or the second through opening of the extramedullary plate is an elongated hole.

According to a further aspect, there is provided a method of fracture fixation of bone, the method comprising the steps of inserting an intramedullary nail into a marrow cavity of bone, wherein the intramedullary nail has a connecting opening defining an axis and a transverse opening configured to receive a bone fastener, inserting a bone fastener through the transverse opening of the intramedullary nail into bone for stabilization of the bone fracture, the inserted bone fastener defining a longitudinal axis, placing an extramedullary plate against the bone, the extramedullary plate having a first through opening and a second through opening, wherein the lateral end of the bone fastener is shoved through the first through opening of the extramedullary plate, and inserting a connecting fastener through the second through opening of the extramedullary plate and the connecting opening of the intramedullary nail to fasten the extramedullary plate to the intramedullary nail and/or to the bone, wherein the axis of the connecting opening of the intramedullary nail is substantially parallel to the longitudinal axis of the bone fastener in an implanted state. Thus, the extramedullary plate can move in a direction substantially parallel to the longitudinal axis of the bone fastener towards the intramedullary nail.

BRIEF DESCRIPTION OF THE DRAWINGS

These and other features, aspects, and advantages of the present disclosure will become more apparent from the following detailed description taken in conjunction with the accompanying drawings, wherein:

FIG. 2a is a top view of an extramedullary plate embodiment shown in FIG. 1;

FIG. 2b is a cross-sectional view of the extramedullary plate embodiment shown in FIG. 2a;

FIG. 4a is a top view of an alternative extramedullary plate embodiment shown in FIG. 3;

FIG. 4b is a cross-sectional view of the alternative extramedullary plate embodiment shown in FIG. 4a;

FIG. 6b is a cross-sectional view of the alternative extramedullary plate embodiment shown in FIG. 5a;

FIG. 8a is a top view of an alternative extramedullary plate embodiment shown in FIG. 7; and FIG. 8b is a cross-sectional view of the alternative extramedullary plate embodiment shown in FIG. 8a;

DETAILED DESCRIPTION

Figure 1:
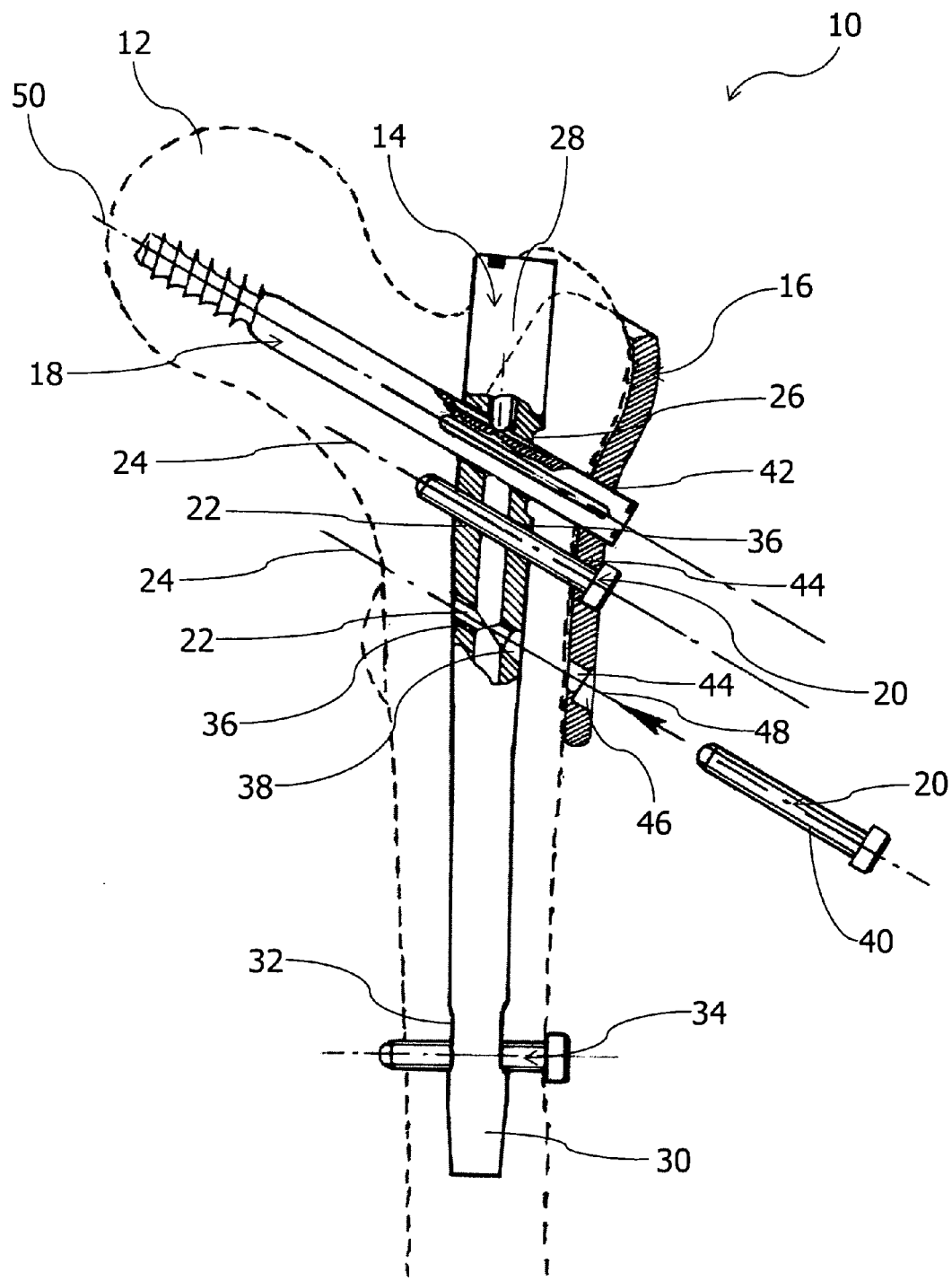
FIG. 1 is a side view of an implant system embodiment.

Referring to FIG. 1, there is shown a side view of an embodiment of an implant system 10 for use in orthopaedic surgery for fixation of bone, such as a femur 12 (schematically illustrated in FIG. 1 by a dashed line). In FIG. 1 only a proximal part of the femur 12 having a femoral neck and a femoral head is shown.

The implant system 10 comprises an intramedullary nail 14, an extramedullary plate 16, a bone fastener 18 and multiple connecting fasteners 20. The intramedullary nail 14 is inserted into a marrow cavity of the femur 12.

The intramedullary nail 14 includes two connecting openings 22 each of which defining a first axis 24, and a transverse opening 26 for receiving the bone fastener 18. The transverse opening 26 and the connecting openings 22 are arranged in a proximal portion 28 of the intramedullary nail 14 and are arranged in an oblique manner relative to a longitudinal axis of the intramedullary nail 14. Further, the intramedullary nail 14 has a distal portion 30 with an opening 32 for receiving a locking screw 34 to fix the intramedullary nail 14 to bone.

The bone fastener 18 (in form of a sliding screw) penetrates the transverse opening 26 of the intramedullary nail 14 and is screwed into the femoral head of the femur 12. The transverse opening 26 of the intramedullary 14 is realized as an elongated hole for enabling sliding of the bone fastener 18 within the transverse opening 26 relative to the intramedullary nail 14. The transverse opening 26 of the intramedullary nail 14 may be realized as a cylindrical hole for enabling sliding of the bone faster 18.

The connecting openings 22 have an internal thread 36 for being engaged by the connecting fasteners 20. The connecting fasteners 20 are realized as locking screws each having a shaft with an external thread 40 that mates with the internal thread 36 of the connecting openings 22. Further, the connecting openings 22 include a conical portion 38 on a side facing the extramedullary plate 16 for an easy inserting of the connecting fasteners 20.

As shown in FIG. 1, the extramedullary plate 16 is anatomically pre-formed in accordance with the shape of the femur 12 and has a first through opening 42 and two second through openings 44. The second through openings 44 of the extramedullary plate 16 each have a receiving portion 46 for receiving the screw head of the connecting fasteners 20. Each of the second through openings 44 of the extramedullary plate 16 defines an axis 48 which is substantially parallel to or congruent with the first axis 24 defined by the connecting opening 22 of the intramedullary nail 14. As illustrated in FIG. 1, the first axes 24 extend in an oblique manner through the extramedullary plate 16.

In the present embodiment, the connecting openings 22 of the intramedullary nail 14, and the first through opening 42 and the second through openings 44 of the extramedullary plate 16 are circular holes.

In the embodiment of the implant system 10 shown in FIG. 1, the bone fastener 18 defines a longitudinal axis 50 and is configured to penetrate the first through opening 42 of the extramedullary plate 16 and the transverse opening 26 of the intramedullary nail 14. The transverse opening 26 of the intramedullary nail 14 defines a second axis 50 which is substantially parallel to or congruent with the longitudinal axis 50 of the bone fastener 18 and which extends in an oblique manner relative to a longitudinal axis of the intramedullary nail 14.

Each of the connecting fasteners 20 is configured to fasten the extramedullary plate 16 to the intramedullary nail 14. As illustrated in FIG. 1, the connecting fasteners 20 are adapted to be inserted through the second through openings 44 of the extramedullary plate 16 and the connecting openings 22 of the intramedullary nail 14. The first axes 24 of the connecting openings 22 of the intramedullary nail 14 are oblique with respect to the longitudinal axis of the intramedullary nail 14 and are substantially parallel to the second axis 50 of the transverse opening 26 of the intramedullary nail 14. Further, the implant system 10 is configured such that the transverse opening 26 of the intramedullary nail 14 can receive the bone fastener 18 within a defined angular range with respect to the longitudinal axis of the intramedullary nail 14. Each of the first axes 24 of the connection openings 22 and the second axis 50 of the transverse opening 26 defines an angle with respect to the longitudinal axis of the intramedullary nail 14. In the present embodiment, the angle may be within an angular range from about 90° to about 150° with respect to the longitudinal axis of the intramedullary nail 14. Thus, the first axis 24 of each connecting opening 22 of the intramedullary nail 14 may be substantially parallel to the longitudinal axis 50 of the bone fastener 18 in an implanted state. Thus, the extramedullary plate 16 can move in a direction substantially parallel to the longitudinal axis 50 of the bone fastener 18 towards the intramedullary nail 14 during and after implantation. Further, the axes of the connecting fasteners 20 are substantially parallel to the longitudinal axis 50 of the inserted bone fastener 18 and/or substantially parallel to the second axis 50 of the transverse opening 26 of the intramedullary nail 14 as well. Thus, during implantation of the extramedullary plate 16 and its connection to the intramedullary nail 14, the extramedullary plate 16 can move freely in the direction of the longitudinal axis 50 of the bone fastener 18 and the longitudinal axis of the connecting fasteners 20.

The first through opening 42 of the extramedullary plate 16 provides for a free sliding of the bone fastener 18 through the extramedullary plate 16. Due to the free sliding of the bone fastener 18 and the guided movement of the extramedullary plate 16 substantially in the direction of the longitudinal axis 50 of the bone fastener 18, a canting or jamming of the extramedullary plate 16 and the fasteners 18 and 22, and particular a jamming of the sliding screw 18, is avoided.

FIG. 2a illustrates a top view and FIG. 2b illustrates a cross-sectional view of the extramedullary plate 16 of the implant system 10 shown in FIG. 1. As illustrated in FIGS. 2a and 2b, the extramedullary plate 16 is anatomically pre-formed. In the present embodiment, the extramedullary plate 16 has an upper curved portion 53a and a lower elongated portion 53b. The extramedullary plate 16 may be adapted to the shape of the greater trochanter.

The extramedullary plate 16 includes the first through opening 42 for receiving the bone fastener 18 and the second through openings 44 for receiving the connecting fasteners 20. The axes 48 of the second through openings 44 are substantially parallel to an axis 52 of the first through opening 42, and all axes 48, 52 extend in an oblique manner through the extramedullary plate 16. Thus, the connecting fasteners 20 can be inserted through the second through openings 44 substantially parallel to the axis 52 of the first through opening 42. In the present embodiment, the first through opening 42 and the second through openings 44 are circular.

Figure 3:
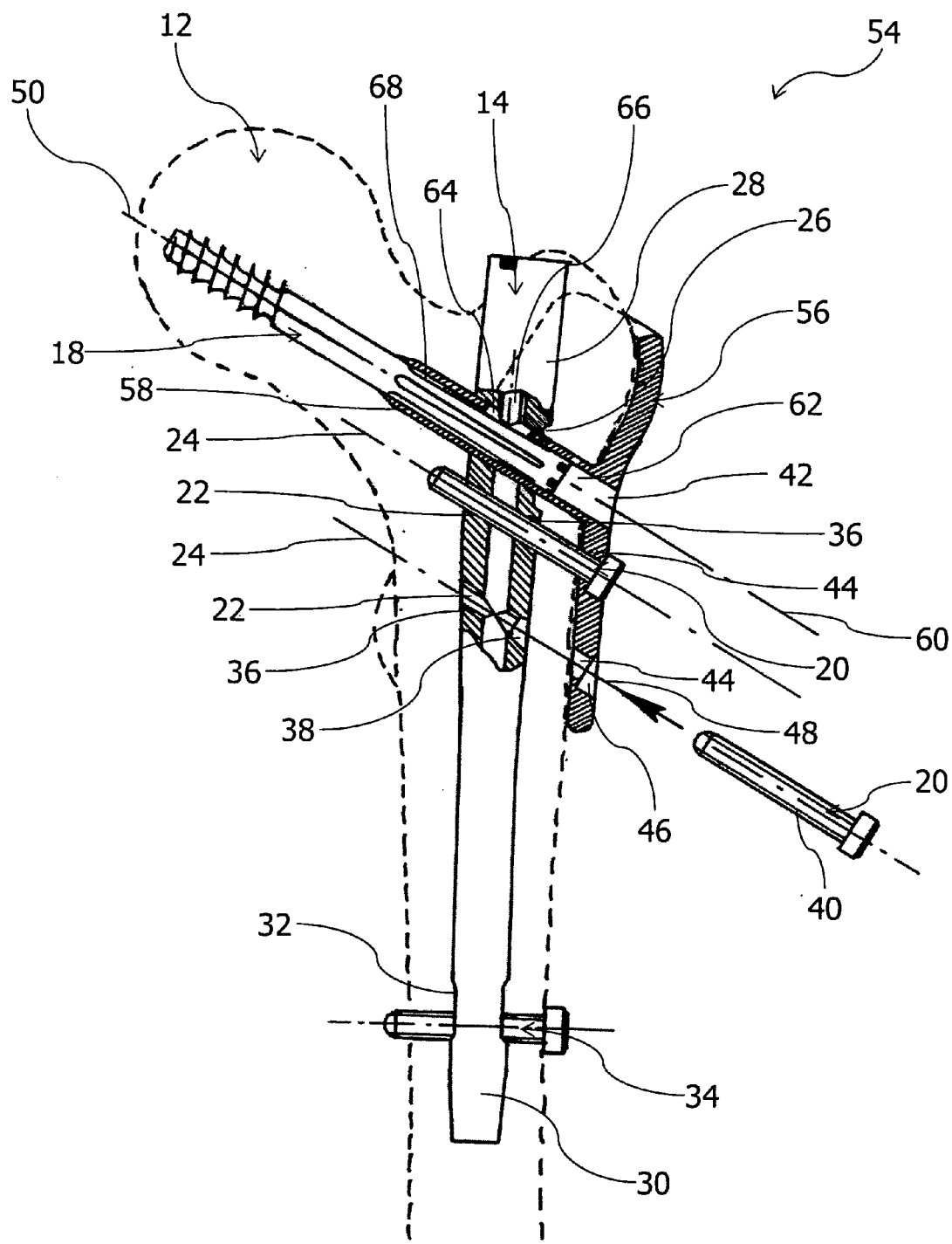
FIG. 3 is a side view of an alternative implant system embodiment.
Figures 4A, 4B:
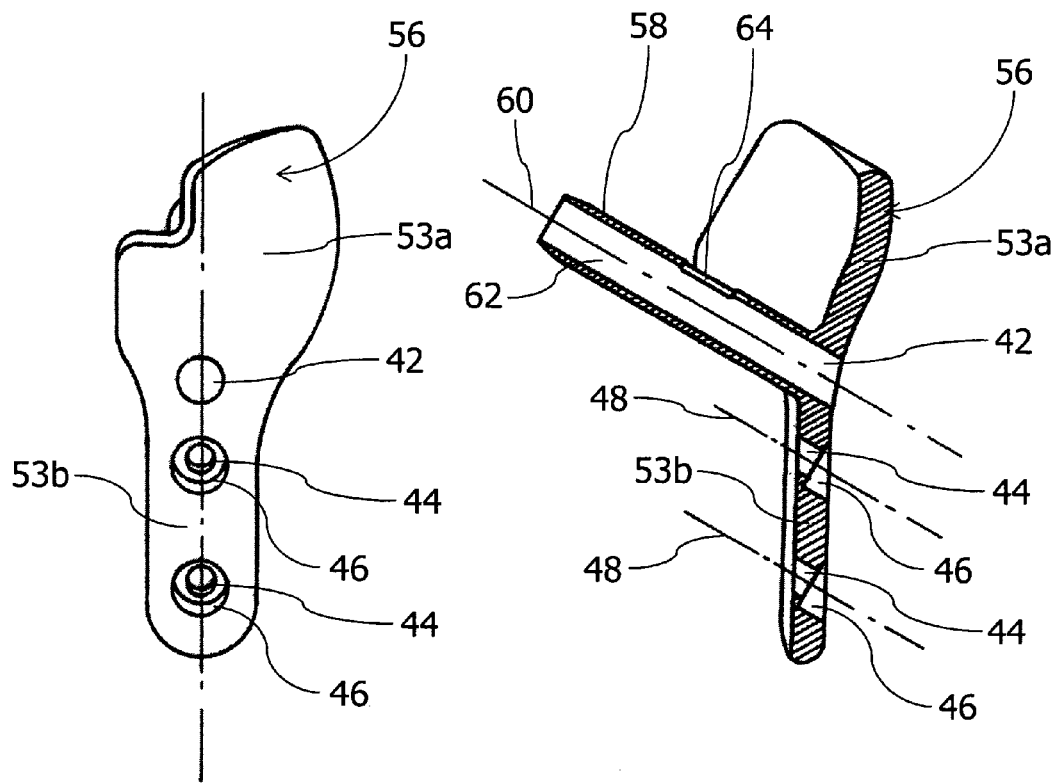

FIGS. 3, 4a and 4b show another embodiment of an implant system 54 with an alternative extramedullary plate embodiment 56.

FIG. 3 is a side view of the alternative implant system 54 comprising the intramedullary nail 14 as shown in FIG. 1 and the alternative embodiment of the extramedullary plate 56. As described above with reference to FIG. 1, the intramedullary nail 14 has a proximal portion 28 including the connecting openings 22 defining the first axes 24 and the transverse opening 26 for receiving the bone fastener 18. The transverse opening 26 defines the second axis 50. The intramedullary nail 14, the extramedullary plate 56, and the fasteners 18 and 20 may be configured as generally described above and hereinafter.

As shown in FIG. 3, the extramedullary plate 56 of the alternative embodiment is anatomically pre-formed and includes the second through openings 44 as described with reference to FIGS. 1 and 2 above. In the present embodiment, the extramedullary plate 56 comprises a guiding structure 58 defining an axis 60 and configured to be received by the transverse opening 26 of the intramedullary nail 14. The axis 60 of the guiding structure 58 is substantially parallel to the longitudinal axis 50 of the bone fastener 18 and/or substantially parallel to the second axis 50 of the transverse opening 26 of the intramedullary nail 14. As shown in FIGS. 3 and 4b, the guiding structure 58 extends in an oblique manner away from the surface of the extramedullary plate 56. The guiding structure 58 includes a hollow portion 62 which is connected to the first through opening 42 of the extramedullary plate 56. As illustrated in FIG. 3, the bone fastener 18 penetrates the guiding structure 58 through a hollow portion 62. Further, the guiding structure 58 has an opening 64 to receive a slidable pin 66. The pin 66 is arranged within the canal of the intramedullary nail 14 to secure the bone fastener 18 relative to the intramedullary nail 14. For this purpose, the slidable pin 66 penetrates the opening 64 of the guiding structure 58 and engages with its tip in a groove 68 of the bone fastener 18.

The hollow portion 62 of the guiding structure 58 allows a free sliding of the bone fastener 18 within the hollow portion 62. As shown in FIG. 3, the guiding structure 58 penetrates the transverse opening 26 of the intramedullary nail 14 and the bone fastener 18 penetrates the hollow portion 62 of the guiding structure 58. Thus, the bone fastener 18 is slidably arranged within the hollow portion 62 of the guiding structure 58. In the present embodiment, the axis 60 of the guiding structure 58 is congruent with the longitudinal axis 50 of the bone fastener 18 as well as with the second axis 50 of the transverse opening 26 of the intramedullary nail 14.

As described above with reference to FIG. 1, the connecting fasteners 20 fasten the extramedullary plate 56 to the intramedullary nail 14, wherein the connecting fasteners 20 are inserted through the second through openings 44 of the extramedullary plate 56 and the connecting openings 22 of the intramedullary nail 14. The first axes 24 of the connecting openings 22 of the intramedullary nail 14 are oblique with respect to the longitudinal axis of the intramedullary nail 14 and are substantially parallel to the second axis 50 of the transverse opening 26 of the intramedullary nail 14. Each of the first axes 24 of the connecting openings 22 and the second axis 50 of the transverse opening 26 defines an angle with respect to the longitudinal axis of the intramedullary nail 14. In the present embodiment, the angle may be within an angular range from about 90° to about 150° with respect to the longitudinal axis of the intramedullary nail 14. Thus, the first axes 24 of the connecting openings 22 of the intramedullary nail 14 are substantially parallel to the longitudinal axis 50 of the bone fastener 18 in an implanted state and the axis 60 of the guiding structure 58 is substantially parallel to the first axes 24 of the connecting openings 22 of the intramedullary nail 14 as well. The extramedullary plate 56 can thus move in a direction substantially parallel to the longitudinal axis 50 of the bone fastener 18 towards the intramedullary nail 14 during and after implantation without jamming. Thus, during implantation of the extramedullary plate 54 and its connection to the intramedullary nail 14, the extramedullary plate 54 can move freely in the direction of the longitudinal axis 50 of the bone fastener 18 and the longitudinal axis of the connecting fasteners 20.

FIG. 4a shows a top view and FIG. 4b shows a cross-sectional view of the alternative extramedullary plate 56 as illustrated in FIG. 3. The extramedullary plate 56 may be configured as generally described above and hereinafter. In the present embodiment, the extramedullary plate 56 includes the upper curved portion 53a and the lower elongated portion 53b. The extramedullary plate 56 may also be adapted to the shape of the greater trochanter. In the present embodiment, the first through opening 42 and the second through openings 44 are circular.

The extramedullary plate 56 also includes the guiding structure 58 with the hollow portion 62 connected to the first through opening 42. Thus, the bone fastener 18 may penetrate the first through opening 42 and the hollow portion 62 of the guiding structure 58. Since the axes 48 of the second through openings 44 of the extramedullary plate 56 are substantially parallel to the axis 60 of the guiding structure 58, the connecting fasteners 20 can be inserted through the second through openings 44, and therewith through the connecting openings 22 of the intramedullary nail 14, substantially parallel to the axis 60 of the hollow portion 62 of the guiding structure 58. Thus, the connecting fasteners 20 can be inserted through the second through openings 44 of the extramedullary plate 56 and through the connecting openings 22 of the intramedullary nail 14 substantially parallel to the longitudinal axis 50 of the bone fastener 18 and/or substantially parallel to the second axis 50 of the transverse opening 26 of the intramedullary nail 14, such that a canting or jamming of the extramedullary plate 56 and the corresponding fasteners 18 and 20 is avoided during implantation.

Figure 5:
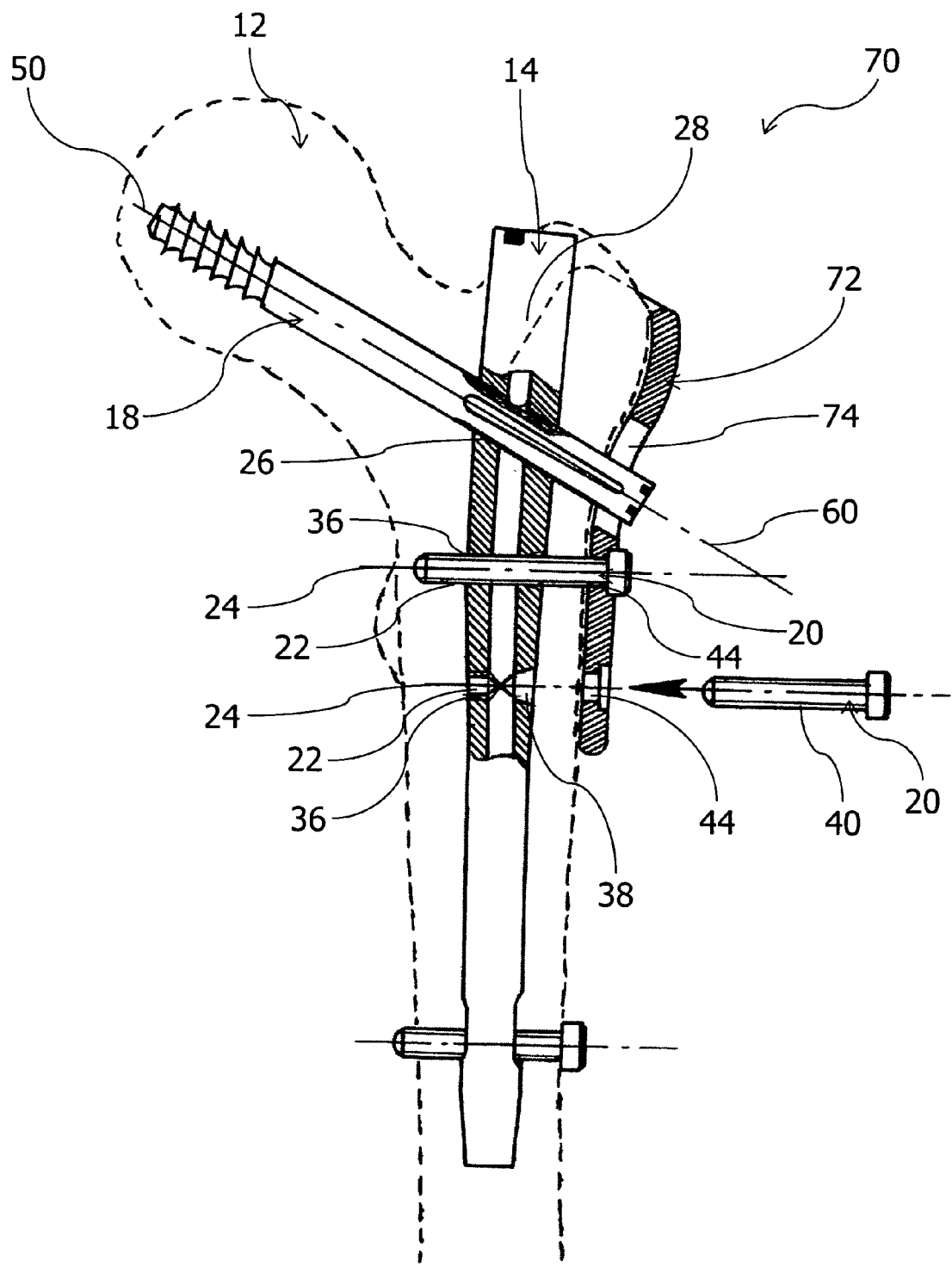
FIG. 5 is a side view of another implant system embodiment.
Figure 6A:
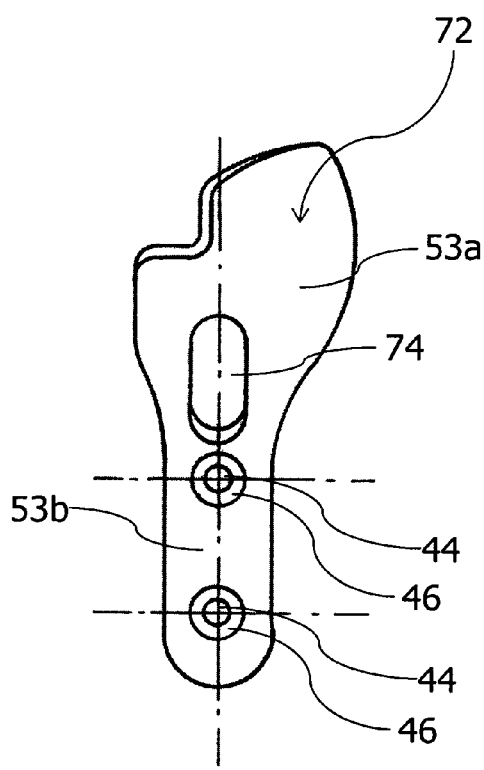
FIG. 6a is a top view of an alternative extramedullary plate embodiment shown in FIG. 5.
Figure 6B:
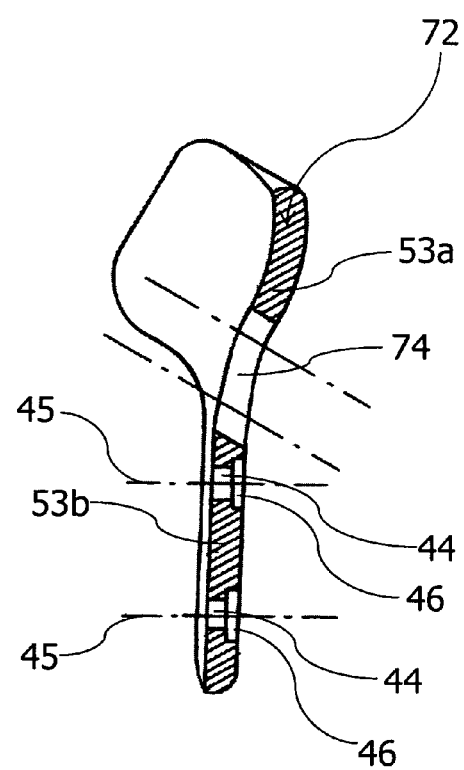

FIGS. 5, 6a and 6b show another embodiment of an implant system 70 with an alternative extramedullary plate embodiment 72.

FIG. 5 is a side view of the implant system 70 comprising an intramedullary nail 14 and the alternative embodiment of the extramedullary plate 72. The intramedullary nail 14, the extramedullary plate 72, and the fasteners 18 and 20 may be configured as generally described above and hereinafter. As described above with reference to FIG. 1, the intramedullary nail 14 has a proximal portion 28 including the connecting openings 22 defining an axis 24 and the transverse opening 26 for receiving the bone fastener 18. The difference between the connecting openings 22 shown in FIG. 5 and the connecting openings shown in FIG. 1 is that the axes 24 of the connecting openings are not parallel to the longitudinal axis 50 of the bone fastener 18 in an implanted state or are not parallel to the axis 50 of the transverse opening 26 of the intramedullary nail 14. In the present embodiment, the axes 24 of the connecting openings 22 are substantially perpendicular with respect to a longitudinal axis of the intramedullary nail 14.

As shown in FIG. 5, the extramedullary plate 72 of the alternative embodiment is anatomically pre-formed and includes the second through openings 44 as generally described with reference to FIGS. 1, 2a and 2b above. Each of the second through openings 44 of the extramedullary plate 72 defines an axis 45 which is substantially parallel to or congruent with the axis 24 of the corresponding connecting opening 22 of the intramedullary nail 14. Thus, the axes 45 of the second through openings 44 of the extramedullary plate 72 may be substantially perpendicular to the longitudinal axis of intramedullary nail 14. As illustrated in FIG. 5, the second through openings 44 of the extramedullary plate 72 as well as the connecting openings 22 of the intramedullary nail 14 may be circular holes. The connecting openings 22 have an internal thread 36 for being engaged by the connecting fasteners 20.

FIG. 6a shows a top view and FIG. 6b shows a cross-sectional view of the alternative extramedullary plate 72 as illustrated in FIG. 5. The extramedullary plate 72 has an upper curved portion 53a and a lower elongated portion 53b. The extramedullary plate 72 may be adapted to the shape of the greater trochanter and may configured as generally described above and hereinafter. In the present embodiment, the extramedullary plate 72 comprises a first through opening 74 which is formed as an elongated hole 74. The elongated hole 74, i.e., the first through opening 74, of the extramedullary plate 72 is defined by a length and a width perpendicular to the length. The length of the elongated hole 74 extends in a direction substantially parallel to a longitudinal axis of the extramedullary plate 72 and the width of the elongated hole 74 extends in a direction substantially parallel to a transverse axis of the extramedullary plate 74 (e.g., an axis perpendicular to the longitudinal axis of the extramedullary plate 74). The length of the elongated hole 74 is greater than the width of the elongated hole 74. The elongated hole 74 may extend in an oblique manner through the extramedullary plate 72 as shown in FIG. 6b. As shown in FIG. 5, the bone fastener 18 penetrates the elongated hole 74 of the extramedullary plate 72 and the transverse opening 26 of the intramedullary nail 14.

As described above with reference to FIG. 1, the connecting fasteners 20 fasten the extramedullary plate 72 to the intramedullary nail 14, wherein the connecting fasteners 20 are inserted through the second through openings 44 of the extramedullary plate 72 and the connecting openings 22 of the intramedullary nail 14. Since the axes 45 of the second through openings 44 of the extramedullary plate 72 are substantially parallel to or congruent with the axes 24 of the connecting openings 22 of the intramedullary nail 14 in an implanted state, and the first through opening 74 of the extramedullary plate 72 is an elongated hole 74, the extramedullary plate 72 can move in a direction substantially parallel to the axis 24 of the connecting opening 22 towards the intramedullary nail 14 without jamming. Thus, a jamming or canting of the bone fastener 18 within the elongated whole 74 of the extramedullary plate 72 and the transverse opening 26 of the intramedullary nail 14 is avoided during implantation.

Figure 7:
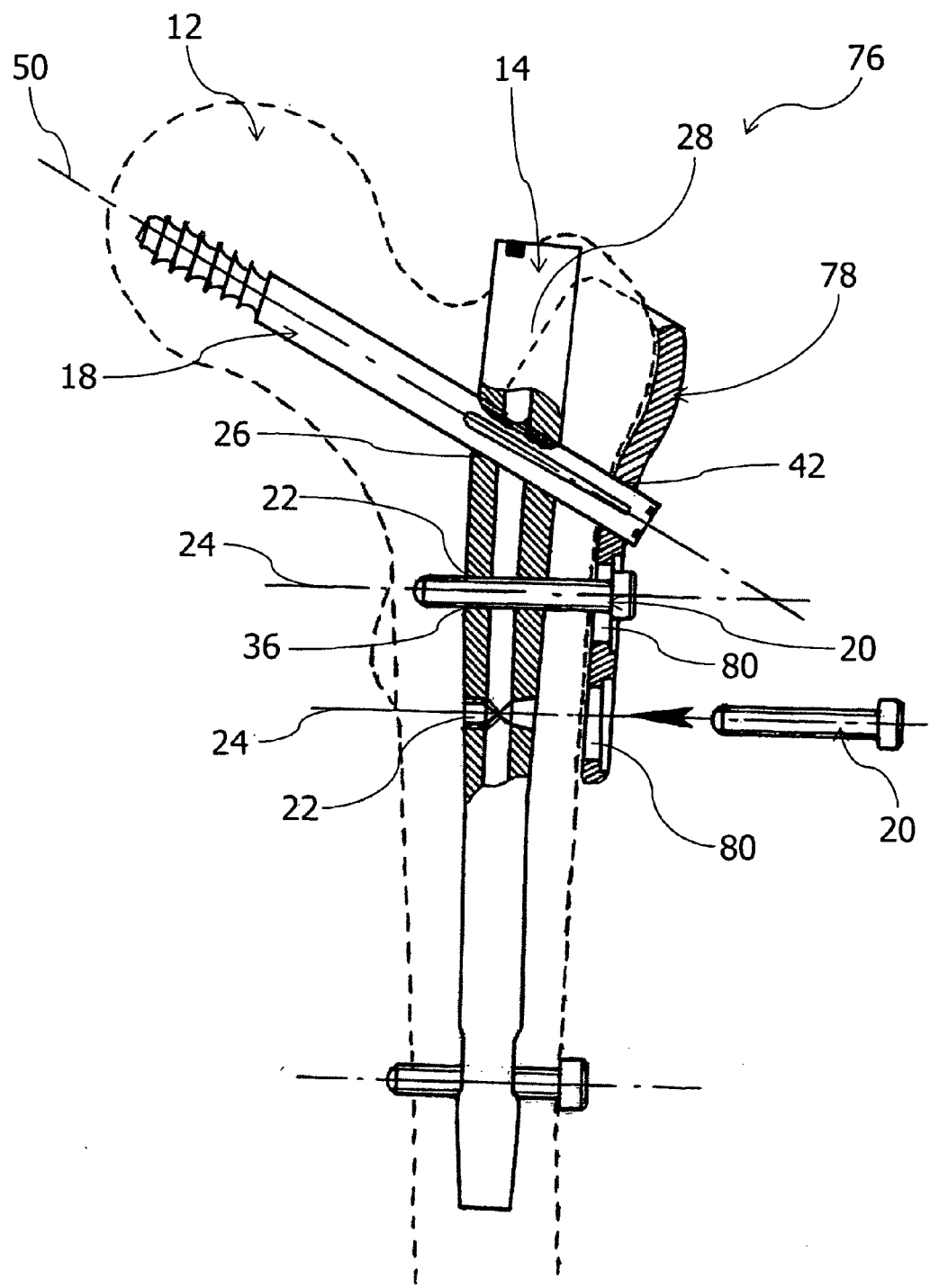
FIG. 7 is a side view of a still further implant system embodiment.
Figures 8A, 8B:
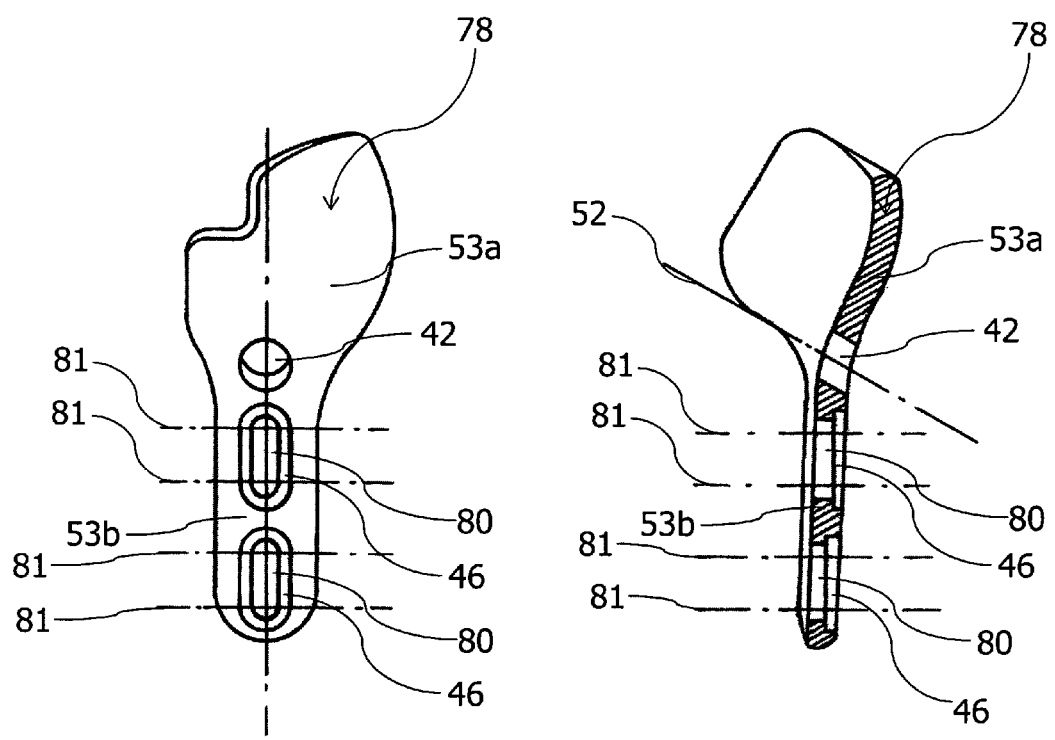

FIGS. 7, 8*a* and 8*b* show another embodiment of an implant system 76 with an alternative extramedullary plate embodiment 78.

FIG. 7 is a side view of the embodiment of the implant system 76. The implant system 76 comprises the intramedullary nail 14 as shown in and as generally described with reference to FIGS. 1 and 5 and the alternative embodiment of the extramedullary plate 78. The intramedullary nail 14, the extramedullary plate 78, and the fasteners 18 and 20 may be configured as generally described above and hereinafter.

As described above with reference to FIGS. 1 and 5, the intramedullary nail 14 has a proximal portion 28 including the connecting openings 22 defining an axis 24 and the transverse opening 26 for receiving the bone fastener 18. The difference between the connecting openings 22 shown in FIG. 7 and the connecting openings shown in FIG. 1 is that the axes 24 of the connecting openings are not parallel to the longitudinal axis 50 of the bone fastener 18 in an implanted state or are not parallel to the axis 50 of the transverse opening 26 of the intramedullary nail 14, as, for example, in the embodiment shown in FIG. 5 as well. In the present embodiment, the axes 24 of the connecting openings 22 are also substantially perpendicular with respect to the longitudinal axis of the intramedullary nail 14.

FIG. 8*a* shows a top view and FIG. 8*b* shows a cross-sectional view of the alternative extramedullary plate 78 as illustrated in FIG. 7. The extramedullary plate 78 has an upper curved portion 53*a* and a lower elongated portion 53*b*. The extramedullary plate 78 may be adapted to the shape of the greater trochanter and configured as generally described above and hereinafter.

As shown in FIGS. 7, 8*a* and 8*b*, the extramedullary plate 78 of the alternative embodiment is anatomically pre-formed and includes the first through opening 42 defining the axis 52 as generally described with reference to FIGS. 1, 2*a* and 2*b* above. The axis 52 of the first through opening 42 extends in an oblique manner through the extramedullary plate 78 as shown in FIG. 8*b*. The first through opening 42 of the extramedullary plate 78 as well as the connecting openings 22 of the intramedullary nail 14 may be circular holes. The connecting openings 21 have an internal thread 36 for being engaged by the connecting fasteners 20.

As further shown in FIGS. 7, 8*a* and 8*b*, the extramedullary plate 78 comprises second through openings 80 which are formed as elongated holes 80. In the present embodiment, the elongated hole 80, i.e., the second through opening 80, of the extramedullary plate 78 is defined by a length and a width perpendicular to the length. The length of the elongated hole 80 extends in a direction substantially parallel to a longitudinal axis of the extramedullary plate 78 and the width of the elongated hole 80 extends in a direction substantially parallel to a transverse axis of the extramedullary plate 78 (e.g., an axis perpendicular to the longitudinal axis of the extramedullary plate 78). Each of the elongated holes 80 of the extramedullary plate 78 defines an axes 81 which may be substantially parallel to or congruent with the axis 24 of the corresponding connecting opening 22 of the intramedullary nail 14. Thus, the axes 81 of the elongated holes 80 of the extramedullary plate 78 may be substantially perpendicular to the longitudinal axis of intramedullary nail 14.

As described above with reference to FIGS. 1 and 5, the connecting fasteners 20 fasten the extramedullary plate 78 to the intramedullary nail 14, wherein the connecting fasteners 20 are inserted through the elongated holes 80 of the extramedullary plate 78 and the connecting openings 22 of the intramedullary nail 14. Since the second through openings 80 of the extramedullary plate 78 are elongated holes 80, the extramedullary plate 78 can move in a direction substantially parallel to the longitudinal axis 50 of the bone fastener 18 towards the intramedullary nail during and after implantation without jamming. Thus, a jamming or canting of the extramedullary plate 78 and the fasteners 18 and 20 is avoided during implantation and the connection to the intramedullary nail 14, since the extramedullary plate 78 can easily move in the direction of the longitudinal axis 50 of the bone fastener 18.

In an exemplary method for fracture fixation of bone, the intramedullary nail 14 is in a first step inserted into the marrow cavity of bone. The intramedullary nail 14 includes the connecting opening 22 defining the first axis 24 and the transverse opening 26 defining the second axis 50 and configured to receive the bone fastener 18.

In a next step, the bone fastener 18 is inserted through the transverse opening 26 of the intramedullary nail 14 into bone for stabilization of the bone fracture.

The extramedullary plate 16 or 56 is then placed against bone. The extramedullary plate 16 or 56 includes the first through opening 42 and the second through opening 44, wherein the lateral end of the bone fastener 18 is shoved through the first through opening 42 of the extramedullary plate 16 or 56.

Finally, the connecting fastener 20 is inserted through the second through opening 44 of the extramedullary plate 16 or 56 and the connecting opening 22 of the intramedullary nail 14 to fasten the extramedullary plate 16 or 56 to the intramedullary nail 14. The first axis 24 of the connecting opening 22 of the intramedullary nail 14 is oblique with respect to the longitudinal axis of the intramedullary nail 14 and is substantially parallel to the second axis 50 of the transverse opening 26 of the intramedullary nail 14. Thus, the extramedullary plate 16 or 56 can move in a direction substantially parallel to the longitudinal axis 50 of the bone fastener 18 and/or substantially parallel to the second axis 50 of the transverse opening 26 of the intramedullary nail 14 towards the intramedullary nail 14 without canting or jamming.

In a further exemplary method for fracture fixation of bone, the intramedullary nail 14 is in a first step inserted into the marrow cavity of bone. The intramedullary nail 14 includes the connecting opening 22 and the transverse opening 26 configured to receive the bone fastener 18.

In a next step, the bone fastener 18 is inserted through the transverse opening 26 of the intramedullary nail 14 into bone for stabilization of the bone fracture.

The extramedullary plate 72 or 78 is then placed against bone. The extramedullary plate 72 or 78 includes the first through opening 42 or 74 and the second through opening 44 or 80, wherein the lateral end of the bone fastener 18 is shoved through the first through opening 42 or 74 of the extramedullary plate 72 or 78.

Finally, the connecting fastener 20 is inserted through the second through opening 44 or 80 of the extramedullary plate 72 or 78 and the connecting opening 22 of the intramedullary nail 14 to fasten the extramedullary plate 72 or 78 to the intramedullary nail 14, wherein the first through opening 74 and/or the second through opening 80 of the extramedullary plate 72 or 78 is an elongated hole 74 or 80. Thus, the extramedullary plate 72 or 78 can move towards the intramedullary nail 14 without canting or jamming as generally described above.

In an further exemplary method for fracture fixation of bone, the intramedullary nail 14 is in a first step inserted into the marrow cavity of bone. The intramedullary nail 14 includes the connecting opening 22 defining the axis 24 and the transverse opening 26 configured to receive the bone fastener 18.

In a next step, the bone fastener 18 is inserted through the transverse opening 26 of the intramedullary nail 14 into bone for stabilization of the bone fracture. The bone fastener 18 defines the longitudinal axis 50.

The extramedullary plate 16 or 56 is then placed against bone. The extramedullary plate 16 or 56 includes the first through opening 42 and the second through opening 44, wherein the lateral end of the bone fastener 18 is shoved through the first through opening 42 of the extramedullary plate 16 or 56.

Finally, the connecting fastener 20 is inserted through the second through opening 44 of the extramedullary plate 16 or 56 and the connecting opening 22 of the intramedullary nail 14 to fasten the extramedullary plate 16 or 56 to the intramedullary nail 14. The axis 24 of the connecting opening 22 of the intramedullary nail 14 is substantially parallel to the longitudinal axis 50 of the bone fastener 18 in an implanted state. Thus, the extramedullary plate 16 or 56 can move in a direction substantially parallel to the longitudinal axis 50 of the bone fastener 18 towards the intramedullary nail 14 without canting or jamming.

While the rod-shaped body of the intramedullary nail includes a distal portion and a proximal portion connected thereto in the embodiments illustrated in the drawings, the nail body can be adapted as needed (e.g., in terms of shape, length, width, thickness, etc.) for use in orthopaedic surgery for fixation of bone and for insertion into an intramedullary canal of, e.g., a femur. Moreover, while the extramedullary plates are anatomically pre-formed to be adapted to the greater trochanter of a femur as illustrated in the drawings, the extramedullary plate can be adapted as needed (e.g., in terms of shape, length, width, thickness, etc.) as well. Thus, the intramedullary nail and the extramedullary plate may be adapted to different applications.

While the bone fastener as described herein is formed as a sliding screw or a lag screw, the bone fastener can be of any type of, e.g., a femoral neck screw or any kind of blade, and can be adapted to different applications as needed. Furthermore, one or more bone fasteners, e.g., two bone fasteners, may be arranged in a constellation as bone fastener 18 shown in and described with reference to FIGS. 1, 3, 5 and 7. In other words, the implant system may have one or more sliding screws arranged as shown in FIGS. 1, 3, 5 and 7. The bone fasteners as well as the connecting fasteners may thus have different diameters, lengths, shapes or threads. Further, the fasteners and the implants described above can generally be made of stainless steel, titanium or any other biocompatible material.

While the above embodiments have exemplarily been described in relation to bone screws, an intramedullary nail and an extramedullary plate, it will be readily apparent that the techniques presented herein can also be implemented in combination with other types of bone fasteners (such as bone pegs having a rod-like or pin-like shaft, wire-like bone fasteners such as Kirschner wires, etc.) as well as other types of implants (such as bone plates, nails, bone distractors, etc.). Accordingly, the present disclosure is not limited to any type of bone fastener or any type of implant.

Due to the fact that the axis of the connecting opening of the intramedullary nail is substantially parallel to the longitudinal axis of the bone fastener, once the bone fastener has been inserted, and/or is substantially parallel to the axis of the transverse opening of the intramedullary nail, such that the extramedullary plate can move in a direction parallel to the longitudinal axis of the bone fastener towards the intramedullary nail, the implant system enables an anatomical treatment of complex trochanteric fractures. Further, a jamming or canting of the plate and the bone fasteners is avoided during implantation, since the extramedullary plate can easily move in the direction of the longitudinal axis of the bone fastener (e.g., a sliding screw) and parallel the longitudinal axis of the connecting fastener (e.g., a locking screw). Thus, a jamming of the sliding screw is avoided. Consequently, the surgical procedure and fixation of the extramedullary bone plate to the intramedullary nail is facilitated. Moreover, a high construct-stability is provided between the bone fasteners, the intramedullary nail and the extramedullary plate connected thereto.

Another advantage of the implant system is the effect that the extramedullary plate works as a fallback device in the case of intramedullary nail breakage. If the intramedullary nail breaks in, e.g., in the area of the sliding screw hole (transverse opening), the distal fragment of the intramedullary nail would transmit all compression forces whereas all tension forces would be transmitted by the extramedullary plate. Such a situation would only result in a very slight varus deformation of the bone fragments depending on the clearance of the sliding screw hole and the stability of the plate connection to the intramedullary nail. Thus, the main function of the intramedullary nail is maintained even in the case of a nail breakage. Moreover, the intramedullary nail as well as the extramedullary plate can easily and cheaply be manufactured with current machine tools and major changes or modifications of the current intramedullary nail design are not required.

The features described in the above description taken in conjunction with the accompanying drawings can be readily combined to result in different embodiments. It will thus be apparent that the present disclosure may be varied in many ways. Such variations are not to be regarded as a departure from the scope of the invention, and all modifications are intended to be included within the scope of following claims.

The invention claimed is:

1. An implant system for use in orthopaedic surgery for fixation of bone, comprising:
   an intramedullary nail with a connecting opening defining a first axis and a transverse opening defining a second axis and configured to receive a bone fastener;
   an extramedullary plate having a first through opening and a second through opening;
   a bone fastener configured to penetrate the first through opening of the extramedullary plate and the transverse opening of the intramedullary nail;
   a connecting fastener configured to fasten the extramedullary plate to the intramedullary nail, the connecting fastener being adapted to be inserted through the second through opening of the extramedullary plate and the connecting opening of the intramedullary nail, wherein the first axis of the connecting opening of the intramedullary nail is oblique with respect to a longitudinal axis of the intramedullary nail and is substantially parallel to the second axis of the transverse opening of the intramedullary nail; and wherein the extramedullary plate comprises at least one guiding structure configured to be received by the transverse opening of the intramedullary nail.

2. The implant system according to claim 1, wherein each of the first axis of the connecting openings and the second axis of the transverse opening defines an angle with respect to the longitudinal axis of the intramedullary nail.

3. The implant system according to claim 1, wherein the connecting opening of the intramedullary nail has an internal thread configured to engage a complementary external thread of the connecting fastener.

4. The implant system according to claim 1, wherein the connecting opening of the intramedullary nail has a conical portion on a side facing the extramedullary plate.

5. The implant system according to claim 1, wherein the second through opening of the extramedullary plate has a receiving portion for receiving a head of the connecting fastener.

6. The implant system according to claim 1, wherein the extramedullary plate is anatomically pre-formed.

7. The implant system according to claim 1, wherein the connecting fastener is a locking screw and/or the bone fastener is a sliding screw.

8. The implant system according to claim 1, wherein the second through opening of the extramedullary plate defines an axis which is substantially parallel to or congruent with the first axis of the connecting opening of the intramedullary nail.

9. The implant system according to claim 1, wherein the second through opening of the extramedullary plate defines an axis that is oblique with respect to a surface region of the extramedullary plate surrounding the second through opening.

10. The implant system according to claim 1, wherein the second axis of the transverse opening of the intramedullary nail is substantially parallel to or congruent with a longitudinal axis of the bone fastener.

11. The implant system according to claim 1, wherein the guiding structure includes a hollow portion and the bone fastener is configured to penetrate the guiding structure of the extramedullary plate through the hollow portion.

12. The implant system according to claim 11, wherein the hollow portion of the guiding structure is connected to the first through opening of the extramedullary plate.

13. The implant system according to claim 1, wherein the guiding structure has an opening configured to receive a set screw or pin.

14. The implant system according to claim 1, wherein the extramedullary plate comprises multiple second through openings.

15. An implant system for use in orthopaedic surgery for fixation of bone, comprising:
    an intramedullary nail with a connecting opening and a transverse opening configured to receive a bone fastener;
    an extramedullary plate having a first through opening and a second through opening;
    a bone fastener configured to penetrate the first through opening of the extramedullary plate and the transverse opening of the intramedullary nail;
    a connecting fastener configured to fasten the extramedullary plate to the intramedullary nail, the connecting fastener being adapted to be inserted through the second through opening of the extramedullary plate and the connecting opening of the intramedullary nail,
    wherein at least one of the first through opening and the second through opening of the extramedullary plate is an elongated hole; and
    wherein the extramedullary plate comprises at least one guiding structure configured to be received by the transverse opening of the intramedullary nail.

16. The implant system according to claim 15, wherein if the first through opening of the extramedullary plate is an elongated hole, the second through opening of the extramedullary plate is a circular hole, or if the second through opening of the extramedullary plate is an elongated hole, the first through opening of the extramedullary plate is a circular hole.

17. The implant system according to claim 15, wherein a first axis of the connecting opening of the intramedullary nail is substantially perpendicular with respect to a longitudinal axis of the intramedullary nail.

18. The implant system according to claim 15, wherein the second through opening of the extramedullary plate defines an axis which is substantially parallel to or congruent with a first axis of the connecting opening of the intramedullary nail.

19. The implant system according to claim 15, wherein the elongated hole of the extramedullary plate is defined by a length and a width, wherein the length extends in a direction substantially parallel to a longitudinal axis of the extramedullary plate and the width extends in a direction substantially perpendicular to the longitudinal axis of the extramedullary plate, and wherein the length is greater than the width.

20. The implant system according to claim 15, wherein the connecting opening of the intramedullary nail has an internal thread configured to engage a complementary external thread of the connecting fastener.

21. The implant system according to claim 15, wherein the connecting opening of the intramedullary nail has a conical portion on a side facing the extramedullary plate.

22. The implant system according to claim 15, wherein the second through opening of the extramedullary plate has a receiving portion for receiving a head of the connecting fastener.

23. The implant system according to claim 15, wherein the extramedullary plate is anatomically pre-formed.

24. The implant system according to claim 15, wherein the connecting fastener is a locking screw and/or the bone fastener is a sliding screw.

25. The implant system according to claim 15, wherein the transverse opening of the intramedullary nail defines a second axis which is substantially parallel to or congruent with a longitudinal axis of the bone fastener.

26. The implant system according to claim 15, wherein the extramedullary plate comprises multiple second through openings.

27. A method of fracture fixation of bone, the method comprising the steps of:
    inserting an intramedullary nail into a marrow cavity of bone, wherein the intramedullary nail has a connecting opening defining a first axis and a transverse opening defining a second axis and configured to receive a bone fastener;
inserting a bone fastener through the transverse opening of the intramedullary nail into bone for stabilization of the bone fracture;
    placing an extramedullary plate against the bone, the extramedullary plate having a first through opening and a second through opening, wherein the lateral end of the bone fastener is inserted through the first through opening of the extramedullary plate and guiding the bone fastener by a guiding structure, the bone fastener configured to penetrate the guiding structure, the guiding structure received by the transverse opening of the intramedullary nail; and inserting a connecting fastener through the second through opening of the extramedullary plate and the connecting opening of the intramedullary nail to fasten the extramedullary plate to the intramedullary nail, wherein the first axis of the connecting opening of the intramedullary nail is oblique with respect to a longitudinal axis of the intramedullary nail and is substantially parallel to the second axis of the transverse opening of the intramedullary nail.

28. A method of fracture fixation of bone, comprising:

inserting an intramedullary nail into a marrow cavity of bone, wherein the intramedullary nail has a connecting opening and a transverse opening configured to receive a bone fastener;

inserting a bone fastener through the transverse opening of the intramedullary nail into bone for stabilization of the bone fracture;

placing an extramedullary plate against the bone, the extramedullary plate having a first through opening and a second through opening, wherein the lateral end of the bone fastener is inserted through the first through opening of the extramedullary plate and guiding the bone fastener by a guiding structure, the bone fastener configured to penetrate the guiding structure, the guiding structure received by the transverse opening of the intramedullary nail; and inserting a connecting fastener through the second through opening of the extramedullary plate and the connecting opening of the intramedullary nail to fasten the extramedullary plate to the intramedullary nail, wherein at least one of the first through opening and the second through opening of the extramedullary plate is an elongated hole.

29. A method of fracture fixation of bone, comprising:

inserting an intramedullary nail into a marrow cavity of bone, wherein the intramedullary nail has a connecting opening defining an axis and a transverse opening configured to receive a bone fastener;

inserting a bone fastener through the transverse opening of the intramedullary nail into bone for stabilization of the bone fracture, the inserted bone fastener defining a longitudinal axis;

placing an extramedullary plate against the bone, the extramedullary plate having a first through opening and a second through opening, wherein the lateral end of the bone fastener is inserted through the first through opening of the extramedullary plate and guiding the bone fastener by a guiding structure, the bone fastener configured to penetrate the guiding structure, the guiding structure received by the transverse opening of the intramedullary nail; and inserting a connecting fastener through the second through opening of the extramedullary plate and the connecting opening of the intramedullary nail to fasten the extramedullary plate to the intramedullary nail, wherein the axis of the connecting opening of the intramedullary nail is substantially parallel to the longitudinal axis of the bone fastener in an implanted state.

* * * * *